(12) United States Patent
Alexander

(10) Patent No.: US 11,596,497 B1
(45) Date of Patent: Mar. 7, 2023

(54) BITE BLOCK WITH A NEEDLE ALIGNMENT ATTACHMENT SYSTEM

(71) Applicant: Arin Alexander, Porter Ranch, CA (US)

(72) Inventor: Arin Alexander, Porter Ranch, CA (US)

( * ) Notice: Subject to any disclaimer, the term of this patent is extended or adjusted under 35 U.S.C. 154(b) by 1016 days.

(21) Appl. No.: 16/365,363

(22) Filed: Mar. 26, 2019

Related U.S. Application Data

(60) Provisional application No. 62/649,450, filed on Mar. 28, 2018.

(51) Int. Cl.
  *A61C 5/00* (2017.01)
  *A61M 5/32* (2006.01)
  *A61M 19/00* (2006.01)
  *A61C 5/90* (2017.01)

(52) U.S. Cl.
  CPC .............. *A61C 5/007* (2013.01); *A61C 5/90* (2017.02); *A61M 5/3287* (2013.01); *A61M 19/00* (2013.01); *A61M 2209/10* (2013.01); *A61M 2210/0631* (2013.01)

(58) Field of Classification Search
  CPC .......... A61C 5/007; A61C 5/90; A61M 19/00; A61M 16/0488; A61M 16/049
  See application file for complete search history.

(56) References Cited

U.S. PATENT DOCUMENTS

| | | | |
|---|---|---|---|
| 2,220,674 A | 11/1940 | Bloomheart | |
| 3,722,101 A | 3/1973 | Via, Jr. | |
| 5,009,595 A | 4/1991 | Osborn | |
| 5,588,836 A | 12/1996 | Landis et al. | |
| 6,241,521 B1 | 6/2001 | Garrison | |
| 6,267,591 B1 | 7/2001 | Barstow | |
| 6,595,962 B1 | 7/2003 | Perthu | |
| 6,716,029 B2 * | 4/2004 | Fischer | A61C 5/90 433/140 |
| 8,251,069 B2 * | 8/2012 | Burdumy | A61C 5/90 433/140 |
| 8,257,341 B1 | 9/2012 | Fletcher | |
| 8,626,317 B2 | 1/2014 | Higgins | |
| 8,911,400 B2 | 12/2014 | Clayton et al. | |

(Continued)

FOREIGN PATENT DOCUMENTS

FR 2858542 A1 2/2005
FR 2942394 A1 8/2010

(Continued)

*Primary Examiner* — Bradley J Osinski

(74) *Attorney, Agent, or Firm* — Stetina Brunda Garred and Brucker; Mark B. Garred

(57) ABSTRACT

A bite block with inclined surfaces fits between a patient's upper and lower jaws to hold them apart and fixes the bite block position relative to the jaws. A support plate slides relative to the bite block to position a needle guide on the support plate along an axis of the support plate. A position stop on the support plate contacts the anterior border of the Ramus of the patient's mandible to position the needle guide along the axis. A syringe needle is guided by the needle guide to a predetermined location to administer anesthetic, preferably to the inferior alveolar nerve as it enters the mandible. The needle guide is inclined to avoid gaging and a tongue depressor attached to the support plate positions the patient's tongue.

20 Claims, 7 Drawing Sheets

(56) References Cited

U.S. PATENT DOCUMENTS

| | | |
|---|---|---|
| 9,486,297 B2 | 11/2016 | Clayton et al. |
| 2008/0058717 A1 | 3/2008 | Spector |
| 2008/0097387 A1 | 4/2008 | Spector |
| 2008/0318183 A1 | 12/2008 | Suzman |
| 2009/0054838 A1 | 2/2009 | Harrison |
| 2011/0244417 A1* | 10/2011 | Hilsen .................. A61M 5/46 433/75 |
| 2014/0356803 A1 | 12/2014 | Clayton et al. |
| 2016/0242885 A1 | 8/2016 | Dickie et al. |
| 2017/0028143 A1 | 2/2017 | Caillieux |

FOREIGN PATENT DOCUMENTS

| | | |
|---|---|---|
| FR | 3031312 A1 | 8/2016 |
| JP | 2001137341 | 5/2001 |
| WO | 2010097520 A1 | 2/2010 |
| WO | 2012139155 A1 | 10/2012 |
| WO | 2015128736 A3 | 9/2015 |

* cited by examiner

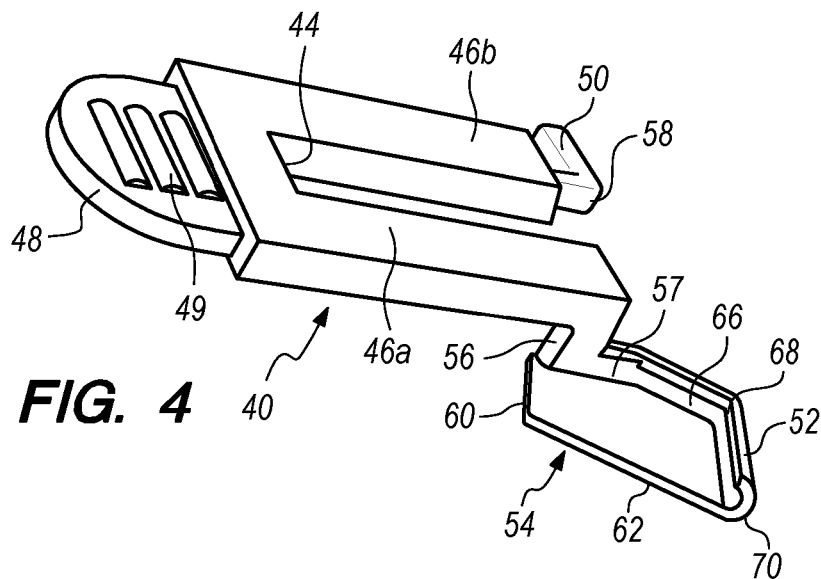
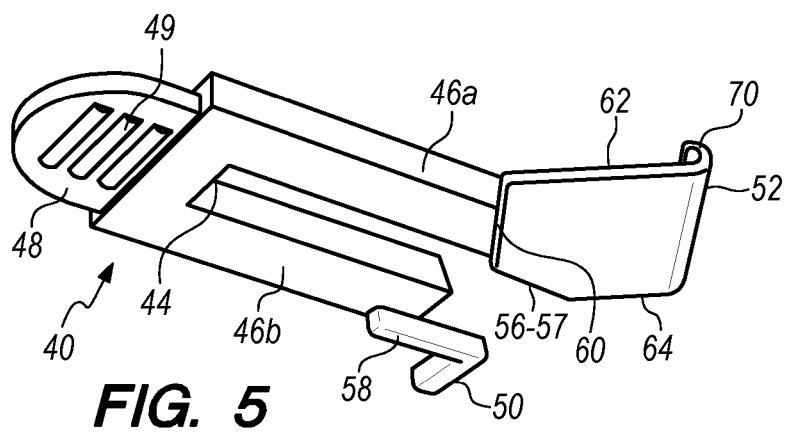
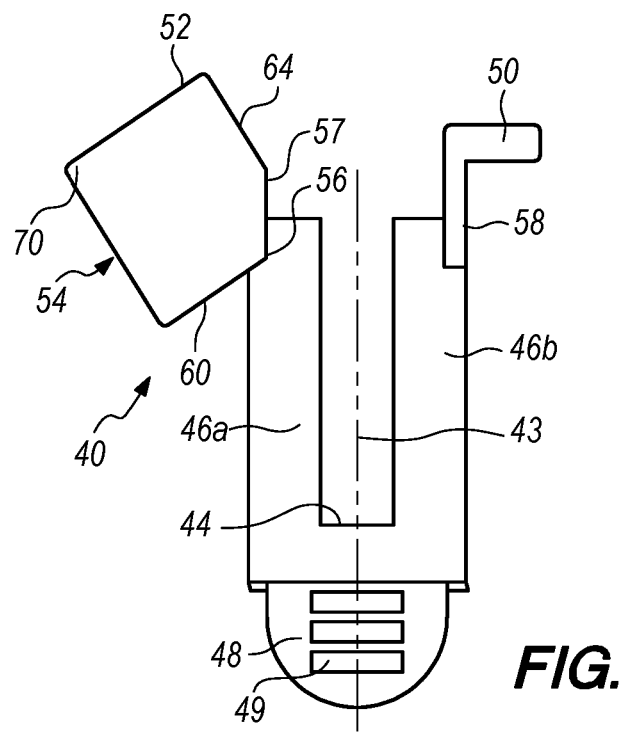

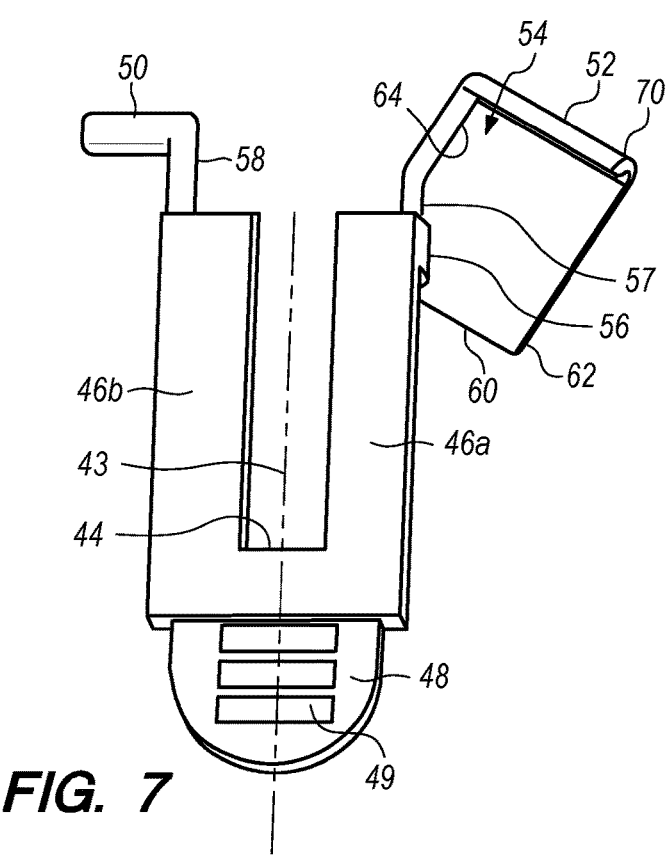
FIG. 7
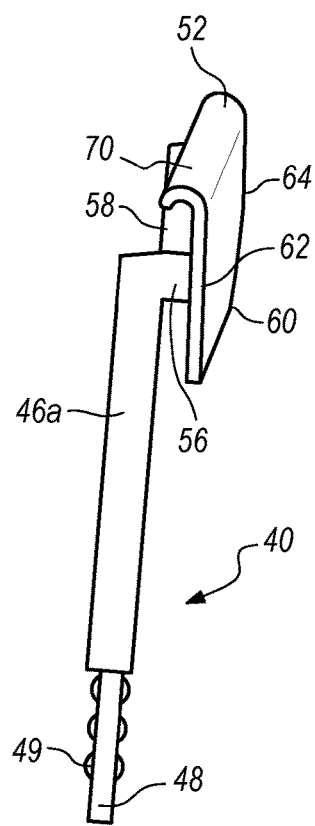
FIG. 8
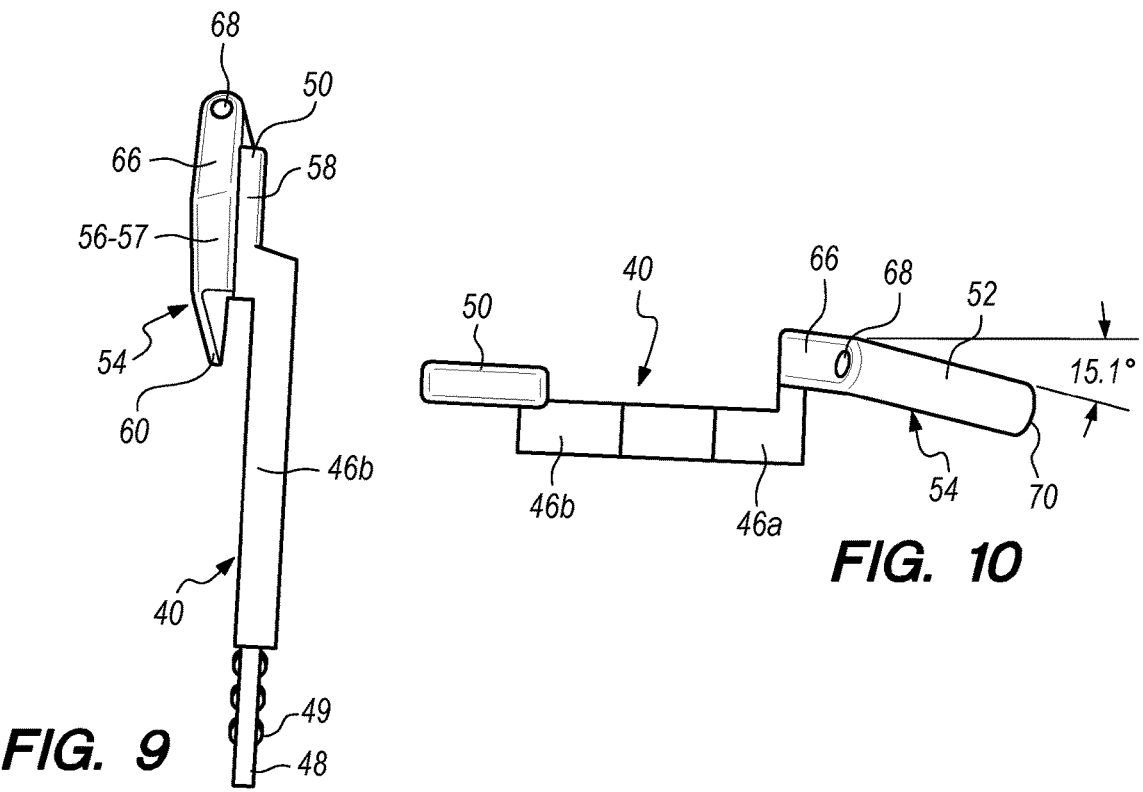
FIG. 9
FIG. 10

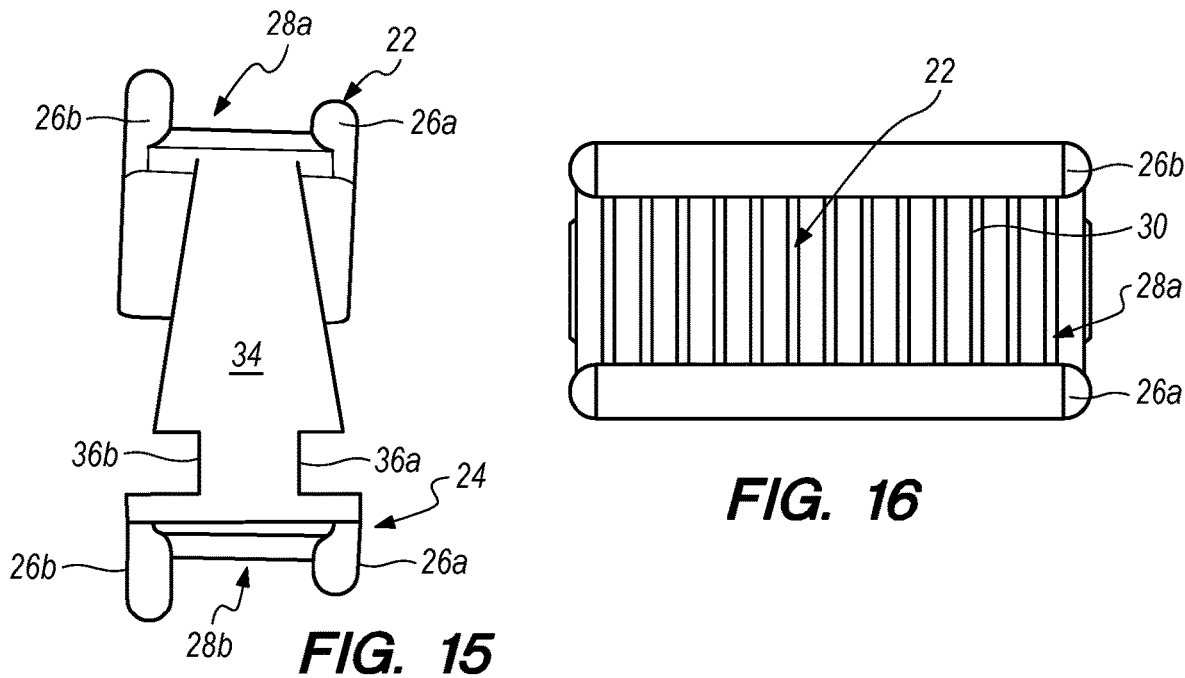
FIG. 15
FIG. 16
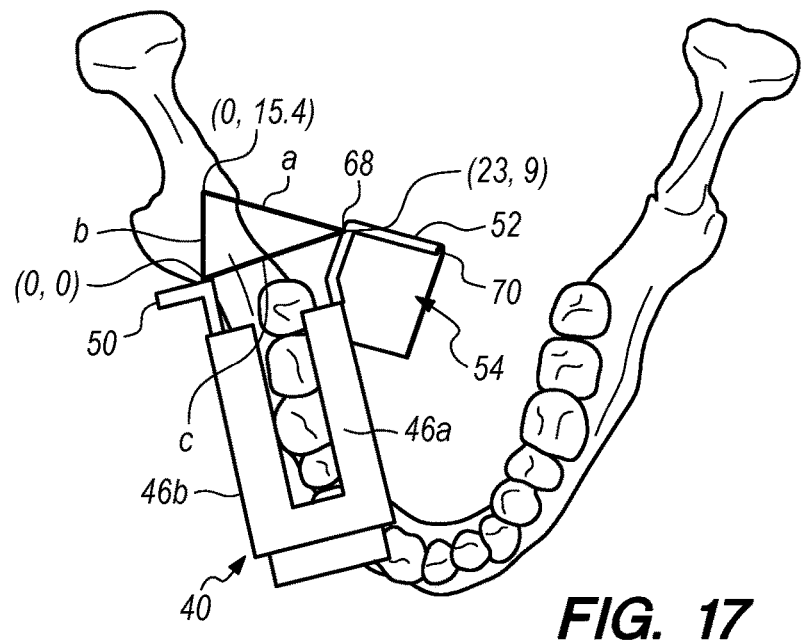
FIG. 17

BITE BLOCK WITH A NEEDLE ALIGNMENT ATTACHMENT SYSTEM

CROSS-REFERENCE TO RELATED APPLICATIONS

The application claims the benefit under 35 U.S.C. § 119(e) to Provisional Patent Application No. 62/649,450 filed Mar. 28, 2018, the entire contents of which are incorporated herein by reference.

BACKGROUND

The present invention relates to a dental method and device for a mandibular block by aligning a needle of an anesthetic syringe relative to a patient's jaw using a bite block with a needle guide.

Local anesthesia is typically administered to numb a patient's relevant nerves before performing various dental procedures on the patient's teeth. For dental procedures on the lower teeth, a nerve block is typically administered to the inferior alveolar nerve within the oral cavity (mouth) of a patient. This nerve block is ideally achieved by inserting the tip of a needle of a syringe within an appropriate distance of the inferior alveolar nerve as it enters the jaw, at the level of the mandibular foramen and injecting an anesthetic. Unfortunately, anatomical variations among patients and differing musculature of the jaw, neck, tongue and mouth make it difficult to accurately locate the inferior alveolar nerve as it enters the jaw in order to place the anesthetic. Errors in accurate placement of the anesthetic can cause insufficient numbing of the alveolar nerve for patient comfort during the dental procedure, can cause unintended numbing of other portions of the oral cavity, and may require excessive medication to achieve the required numbness to perform the dental procedure. There is thus a need for a method and apparatus to accurately place the needle tip of a syringe for an inferior alveolar nerve block in the mandible.

Dental patients may move their jaw as the anesthesia needle is positioned and the anesthetic administered and this may cause difficulty in maintaining accurate positioning of the needle tip relative to the patient's moving head. Bite blocks are known that wedge between the upper and lower teeth on one side of the patient's jaw, such as disclosed in U.S. Pat. Nos. 2,220,674, 6,716,029 and 5,009,595. These bite blocks limit some movement of the upper and lower jaw and maintain an open mouth for a more consistent access to the oral cavity. But these bite blocks are typically used when performing dental procedures on the teeth and not when the anesthetic is administered. There thus remains a need for an improved method and apparatus to restrain a patient's jaw movement and to locate and/or guide needles to the inferior alveolar nerve to administer a nerve block.

Prior art methods and devices attempt to locate the needle tip by various means. The Gow-Gates technique uses the dentist's hands to locate parts of the patient's ear (intertragic notch), mouth and use those landmarks along with the angle of the ear to the side of the face and the location of mesiopalatal cusp of second maxillary molar to select the location for inserting the needle tip. Unfortunately, this technique produces inconsistent results, especially when first learning the technique, and typically numbs a larger portion of the patient's jaw, tongue and mouth than does administration of a smaller amount of anesthetic to the inferior alveolar nerve. There is thus a need for an improved method and apparatus to more accurately and consistently administer a nerve block to the inferior alveolar nerve, and to restrain movement of the patient's jaw.

Moreover, many dentists will pull the patient's mouth sideways while manually contacting the patient's jaw and ear to manually detect guideposts to estimate a position for the needle, while using the syringe to pull against the other side of the patient's mouth to make the needle enter as perpendicular as possible to the mandible. But unfortunately, patient's mouths are seldom wide enough and flexible enough to align the needle perpendicular to the selected portion of the mandible, and stretching the mouth to better align the needle causes patient distress and movement. The result is that the needle may be inserted at an angle along the mandible so the needle passes through a length of the patient's tissue and that inclined passage of the needle through the tissue makes it difficult to accurately place the needle tip to administer the anesthetic, especially if the patient moves his or her jaw or mouth during the procedure. There is thus a need for an improved method and apparatus to more accurately and consistently administer a nerve block to the inferior alveolar nerve, and to restrain movement of the patient's jaw.

Syringes with curved or angled needles have been provided, as reflected to published patent application numbers 2008/0058717 and 2008/0097387, and it is believed that some dentists manually bend needles to their desired angles for use. But while these curved or angled needles reduce the need to stretch the patient's mouth to position the needle, they do not improve on the accuracy in locating the tip of the needle to administer the anesthetic nor do they reduce inaccuracies in positioning arising from moving the patient's jaw or mouth. The resulting syringes are also believed more costly to use than conventional syringes and needles. There is thus a continued need for an improved method and apparatus to more accurately and consistently administer a nerve block to the inferior alveolar nerve, and to restrain movement of the patient's jaw.

Efforts to mechanize the Gow-Gates technique have been attempted as reflected by WO 2012/139155. A device resembling a C-clamp has a portion external to the oral cavity with a light source aligned with the needle so that when the light is aligned with the desired portion of the patient's body outside the oral cavity to guide insertion of the needle inside the oral cavity. This apparatus attempts to use a light to position the needle relative to an extra-oral landmark on the patient, rather than the using the dentist's fingers to do so. This apparatus is still affected by anatomical variations and variations in the musculature of the tongue, jaw and mouth and is affected by the user's ability to align the light at the correct location on the patient's face. There is thus a continued need for more precisely locating the needle of a syringe to more accurately and consistently administer a block to the inferior alveolar nerve, and to restrain movement of the patient's jaw.

U.S. Pat. No. 8,257,341 describes a method and apparatus that uses a guide curved to fit the anterior border of the Ramus of the mandible in the most concave curve leading to the coronoid process, referred to as the coronoid notch. Multiple holes or slots in the shaped guide plate allow needles to be placed in various locations to administer the nerve block. But the selection of which hole or slot to use and the angle of the needle's insertion through the selected hole or slot are uncontrolled and result in variations. Administering multiple shots through multiple holes or slots risks overmedicating the patient and unnecessary numbing. The localized abutment of the shaped guide with the coronoid process is believed uncomfortable for the patient and the guide is located at the fulcrum of the jaw so that tightening of the jaw during the shot squeezes the shaped guide and may cause patient discomfort. Variations in the orientation of the guide and handle may result in varying the location of the holes and slots through which the needle may be inserted. There is thus a continued need for an improved method and apparatus to locate and/or guide needles to a location adjacent the inferior alveolar nerve to administer a nerve block, and to restrain movement of the patient's jaw.

BRIEF SUMMARY

A bite block with inclined surfaces fits between a patient's upper and lower jaws to hold them apart and fixes the bite block position relative to the jaws. A support plate slides relative to the bite block to position a needle guide on the support plate along an axis of the support plate. A position stop on the support plate contacts the anterior border of the Ramus of the patient's mandible to position the needle guide along the axis relative to the position stop and a predetermined location of the mandibular foramen on an average jaw. Because the configuration of the bite block and support plate are known, the location of the position stop on the support plate allows the needle axis extending along the needle guide (also on the support plate) to be oriented so it intersects the desired location on the mandible. A syringe needle is guided by the needle guide to a predetermined location on the inside of the mandible to administer anesthetic, preferably to the inferior alveolar nerve as it enters the mandible at the mandibular foramen.

More specifically, the location of the mandibular foramen is determined relative to the anterior border of the Ramus at the occlusal plane, preferably at the outer side of the mandible, based on an average of measurement of mandibles from skeletons. The bottom of the position stop is aligned with the lower teeth engaging portion of the bite block so the position stop hits the anterior border of the Rambus at the occlusal plane, preferably at the outer side of the mandible. Because the needle guide and position stop are on the same part, their relative position is known and that allows an axis extending along the needle guide to be located and oriented to intersect the predetermined location of the mandibular foramen. In short, correctly placing the position stop aligns the needle guide with the predetermined location of the mandibular foramen. A left and right version of the bite block, position stop and needle guide are used for the left and right sides of the mandible.

The desired location for administering the anesthetic is located far enough back in the mouth and low enough on the mandible that inserting the needle perpendicular to the mandible at the desired location will cause gaging and also likely cause the needle tip to hit the tongue. The needle guide is thus advantageously inclined and offset from the mandible to avoid gaging and a tongue depressor may be attached to the support plate and also inclined to position the patient's tongue to avoid the needle's path and to help avoid gagging. The tip of the needle is advantageously bent sideways so the bent needle tip may be easily positioned against the needle guide and moved along the needle guide to position the needle relative to the mandible to administer the anesthetic—without distorting the patient's cheek and without causing gaging.

A method and apparatus are provided for aligning a needle tip with the mandibular foramen for administering a nerve block via an aesthetic through the needle, to numb the inferior alveolar nerve. A bite block is positioned on the side of the patient's mouth to which the nerve block is to be administered. The bite block has a general wedge shape with an upper and lower teeth engaging surface inclined toward each other and inclined toward an interior juncture that is positioned toward the interior of the user's jaw during use, adjacent the anterior border of the Ramus of the mandible. The upper and lower teeth engaging portions are preferably held apart by a wall having the shape of a triangular segment which is narrower at a top side and wider at a bottom side of the wall and the bite block. Advantageously, the top tooth engaging surface may have a U-shaped cross-section with opposing inner and outer side flanges oriented to extend along the respective inner and outer sides of the crown of the teeth and a ribbed bottom to abut the respective, grinding portion of the teeth. Advantageously, the bottom tooth engaging surface may have an inverted, downwardly facing, U-shaped cross-section with opposing inner and outer side flanges along the respective inner and outer sides of the crown of the teeth and a ribbed bottom to abut the respective, grinding portion of the teeth. Advantageously, the outer flange is slightly longer than the opposing, inner flange so as to extend further along the outer side of the crown of the teeth and toward the immediately adjacent gums than the opposing, inner flange. The bite block and especially the upper and lower teeth engaging portions align the bite block relative to the patient's teeth and jaw which clamp against the bite block and hold the bite block in position.

The bite block has a needle guide connected to an inside, back portion of a support plate that is movably connected to the bite block to position the needle guide relative to the bite block. The needle guide may advantageously also include a tongue depressor.

The support plate advantageously has two support arms configured to engage and slide along alignment slots formed in the wall joining the upper and lower teeth engaging portions in order to guide and position the needle guide. The wall slots extend along and preferably immediately adjacent to the lower teeth engaging surface, on opposing sides of the wall. The alignment slots advantageously extend the entire length of the bite block. The support arms preferably form a slot between them, which slot opens onto the back end of the support plate, with the front end of the arms joined to abut the front end of the wall on the bite block to limit the maximum insertion of the support plate relative to the bite block. Thus, the alignment slots and support arms interlock to position the support plate relative to the bite block, and to thereby position the needle guide connected to the back end of the support plate.

A positioning stop extends outward from a back end of the support plate to abut the jaw at the anterior border of a Ramus of the mandible below the coronoid process. The position stop locates or positions the support plate a predetermined distance from the anterior border of the Ramus of the patient's jaw, with the bite block and support plate orienting and aligning the support plate with the patient's teeth and jaw, and also orientating and aligning the needle guide with the desired location for administering the anesthetic. The position stop may extend outward and either upward or downward from the end of the support plate, depending in part on the construction of the support plate and the location of the alignment slots. When the support arms and alignment slots are just above the lower teeth engaging surface, the position stop extends outward and is located below the back end of the outer support arm.

Advantageously, the support plate is inserted into the alignment slots after the bite block is positioned in the user's oral cavity or mouth. A handle on the front end of the support plate may help insert, position and remove the support plate and the dentist or user may manually urge the support plate into the patient's mouth to keep the position stop against the anterior border of the Ramus during administration of the anesthetic.

A needle guide and tongue depressor are connected to an interior end of the support plate, toward the medial plane and more specifically are connected so the needle guide is inclined downward, rearward and outward to intersect the desired location on the inside of the mandible. The tongue depressor may comprise a plate and is shown as a generally rectangular plate having an adjustment arm at one corner of the plate connecting the tongue depressor plate to the inner support arm. The tongue depressor may be canted diagonally relative to the length of the inner support arm to reduce the amount of the tongue depressor located in the back of the mouth to help reduce gagging. A flange, preferably an upwardly curved flange with opposing, open ends, extends along an interior side of the tongue depressor plate with the curved flange forming the needle guide that extends along an axis that intersects the mandibular foramen during administration of the anesthetic.

The curved flange forming the needle guide may be aligned at an angle of about 105° to the medial or sagittal plane and at an angle of about 15° downward from the traverse plane through the needle opening in the protective flange so that the needle guide aligns with the end of the mandibular foramen, preferably with the end of the mylohyoid grove. The resulting location on the mandible is believed to be the preferred location for most adults based on an analysis of adult mandibles.

The needle guide axis is believed to intersect the patient's opposing cheek at a location that makes it uncomfortably difficult for most patients to allow a syringe with a straight needle to be placed at the side of the patient's mouth and aligned with the needle guide. Bending the needle tip avoids trying to manually stretch the patient's mouth to place the syringe and administer the anesthetic, and avoids the costly, specialized syringe used to administer shots with a needle perpendicular to the syringe plunger. The downward angle allows the patient's tongue to assume a position that avoids if not reduces gaging when the needle guide and tongue depressor are in position to administer the anesthetic. The shortest path through the patient's mandible tissue to the mandibular foramen would be perpendicular to the mandible, but placing a needle to achieve that shortest-path approach is believed to cause gagging and may well result in poking the patient's tongue with the needle to administer the anesthetic. The needle guide aligns the syringe needle along an axis that is believed to avoid gagging and also reduces the likelihood of poking the patient's tongue and is thus a compromise to accommodate patient comfort.

In use, the bite block is wedged between the patient's teeth and the support plate is inserted into the alignment slots of the bite block so the wall of the bite block fits into the slot between the support arms to interlock the support plate to the bite block. The support plate is positioned so the tongue is below the tongue depressor and the position stop contacts the anterior border of the Ramus of the patient's jaw. This should align the needle guide. A needle with its distal end bent about 90° to form a bent end of the needle is inserted along the support block and tongue depressor until the bent end of the needle is at or abutting the needle guide. The bent end of the needle is then aligned along and moved along the needle guide and into the patient's gum to administer the anesthesia. A needle other than 90° is still accommodated by the needle guide because the bent needle tip is aligned by contacting the tip with the guide. Advantageously the tip of the needle is inserted until it abuts the mandible and is then backed off slightly (e.g., a mm or less) before the anesthetic is administered. After administering the anesthetic, the support plate and bite block are removed and autoclaved for reuse, or discarded, although the bite block may remain in the patient's mouth or reinserted in the patient's mouth after the support plate is removed if the dentist wants to use the bite block to maintain the patient's teeth in an open position.

In more detail, there is provided a dental apparatus for aligning a needle tip of a syringe to administer an anesthetic in the oral cavity of a patient having a mandible with teeth thereon. The dental apparatus may include a bite block having upper and lower teeth engaging surface inclined at an angle to each other and oriented in opposing directions so as to engage a substantial portion of the upper and lower teeth, respectively, when inserted between the teeth on one side of the patient's jaws during use. The bite block may also include two alignment slots extending along a length of the bite block with each slot being on an opposing side of the bite block and located above the tooth engaging surface. The apparatus may also include a support plate having a front end with first and second, spaced apart support arms extending rearward and parallel to each other, and located so each support arm can engage and slide along a different one of the alignment slots at the same time. Each support arm advantageously has substantially the same length and further has a rear end. The support plate has a position stop extending laterally and outward from the first support arm at a location that is behind the rear end of that first support arm. The support plate also has a needle guide connected to the second support arm and extending along a needle axis. The needle guide and needle axis may extend toward a location behind a back end of the support plate at an angle to a vertical plane between the length of the support arms when measured in a traverse plane which is orthogonal to the vertical plane and passing through a centerline of at least one of the support arms. The needle guide and needle axis also extend downward at an angle relative to the traverse plane.

In further variations, the dental apparatus may include a tongue depressor having a plate connected to a lower portion of the needle guide and extending forward of the needle guide. The support plate may have a handle on the front end of the support plate. An inner flange and an outer flange may be located on opposing sides of each tooth engaging surface, with the flanges oriented to extend along the patient's teeth during use and short enough not to abrade the patient's gums during use. The bite block may have a wall extending in the vertical plane and with the alignment slots formed in opposing sides of that wall. Each support arm advantageously has a generally rectangular cross-section and the alignment slots have a mating size and cross-sectional shape. Instead of being separated parts, the support arms may be located in the alignment slots of the bite block with the needle guide and needle axis oriented to extend outward away from the sagittal plane during use, to extend downward toward the mandible during use, and to extend backward toward a location between the anterior and posterior borders of the Ramus during use. The support plate may have a support plate stop extending between the two support arms and located to abut an end of the wall during use to limit relative movement of the support plate relative to the bite block in the rearward direction during use.

In still further variations, a tongue depressor is provided having a plate connected to a lower portion of the needle guide and extending forward of the needle guide. The tongue depressor may have an inner flange and an outer flange on opposing sides of each tooth engaging surface, with the flanges oriented to extend along the patient's teeth during use. Additionally, the wall may extend along the vertical plane and the alignment slots may be formed in opposing sides of that wall and extend in the transverse plane. A support stop may extend between the two support arms and is advantageously located to abut an end of the wall during use to limit relative movement of the support plate relative to the bite block in the rearward direction during use.

There is also advantageously provided a dental apparatus for aligning a needle tip of a syringe with a patient's mandible to administer an anesthetic to the patient. This apparatus may include a bite block having an upper and lower teeth engaging surface inclined at an angle to each other and facing in opposing directions. The tooth engaging surfaces are advantageously in a first plane. A wall extends along the first plane and is connected to at least the lower teeth engaging surface. Two alignment slots extend along a length of the bite block and parallel to the lower teeth engaging surface and are located on opposing sides of the wall. This apparatus also has a support plate with first and second, spaced apart support arms each configured to engage and slide along a different one of the alignment slots, where each support arm has a length. A position stop extends outward from a rear portion of the first support arm and extends a distance sufficient to engage an anterior border of the patient's Ramus during use. A needle guide is connected to the second support arm along a needle axis inclined toward the rear of the support plate and inclined downward relative to the support plate.

In further variations of this apparatus, a tongue depressor plate is connected to a lower side of the needle guide and extends forward of the needle guide. The tongue depressor plate may have an upper surface with an outer flange extending above the upper surface along an outer length of the tongue depressor and extending to the needle guide. The outer flange does not block the needle guide so a needle may pass through the needle guide during use. A handle may connect to a forward end of the support plate. Each of the two support arms is advantageously placed in a different one of the alignment slots, with the needle guide extending outward away from the first plane, and extending in a direction downward below the support plate, and also extending in a backward direction. The needle guide may also advantageously offset below a bottom, back end of the second support arm by an adjustment arm.

There is also advantageously provided a method for administering an anesthetic to a mandible, the method including the step of placing a bite block in a patient's mouth where the bite block has opposed and inclined upper and lower surfaces to engage the patient's teeth and maintain the teeth inclined at an angle. The bite block may have at least an inner and outer alignment slot on respective inner and outer sides of the bite block. The method further includes inserting respective inner and outer support arms of a support plate into the respective inner and outer alignment slots on the bite block and advancing the support plate and support arms along a length of the bite block and alignment slots until a position stop connected to a rear end of the outer support arm abuts the anterior border of the Ramus of the patient's mandible. The inner support arm has a needle guide connected to a rear end of the inner support arm so as to orient the needle guide along an axis oriented rearward, outward and downward toward an area between the anterior and posterior borders of the Ramus. The step of advancing the support plate also advances the inner support arm and the needle guide further into the patient's mouth. The method also includes placing a length of a needle tip along the needle guide while manually urging the positioning stop against the anterior border of the Ramus. The method also includes moving the length of the needle tip along the needle guide until the needle hits or is immediately adjacent to the mandible and injecting anesthetic through the tip of the needle.

In further variations, a needle axis extends along the needle guide and the step of advancing the position stop until it abuts the anterior border of the Ramus also positions that needle axis to intersect the mandibular foramen of the patient. The moving step advantageously moves the length of the needle tip along the needle guide until the tip of the needle abuts the mandible. The method may also include moving the tip of the needle slightly away from the mandible and injecting the anesthetic. The needle guide may be located on an upper surface of a tongue depressor and along an inner surface of that tongue depressor, and the step of positioning the needle guide also positions the tongue depressor to allow a needle axis extending along the needle guide to intersect the mandible without intersecting the patient's tongue. The method variations also include bending the tip of the needle about 90° and the step of placing the tip of a needle along the needle guide includes placing the bent tip of the needle along the needle guide. The method may also include removing the support plate from the bite block, removing the bite block from the patient's oral cavity and autoclaving the support plate and bite block for reuse with another patient.

There is also provided a dental apparatus for aligning a needle tip of a syringe to administer an anesthetic in the oral cavity of a patient having a mandible with teeth thereon. The apparatus includes a bite block having upper and lower teeth engaging surface inclined at an angle to each other and oriented in opposing directions so as to engage a portion of the upper and lower teeth, respectively, when inserted between the teeth on one side of the patient's jaws during use. The apparatus further includes a support plate having a front end with first and second, spaced apart support arms extending rearward during use and parallel to each other. The bite block may include two alignment guides extending along a length of the bite block with each alignment guide being on an opposing side of the bite block. Each support arm advantageously includes a mating alignment guide that mates with and moves along a different one of the alignment guides. Each support arm has a rear end. The apparatus includes a position stop extending laterally and outward from the first support arm at a location that is behind the rear end of that first support arm. A needle guide is connected to the second support arm and extends along a needle axis, and when the alignment guides and mating alignment guides are in mating engagement the needle guide and needle axis extend outward away from the sagittal plane, extend downward toward the mandible, and extend backward toward a location between the anterior and posterior borders of the Ramus.

In further variations of this dental apparatus, the needle axis and needle guide are aligned to intersect a predetermined location of a mandibular foramen. Additionally, the apparatus may include a tongue depressor having a plate connected to a lower portion of the needle guide and extending forward of the needle guide. A handle is advantageously provided on the front end of the support plate. A support plate stop may extend between the two support arms and be located to abut a portion of the bite block to limit relative movement of the support plate relative to the bite block in the rearward direction when the alignment guides and mating alignment guides are in mating engagement. The alignment guides and mating alignment guides are preferably in mating engagement during use. The apparatus may have an inner flange and an outer flange on opposing sides of each tooth engaging surface, with the flanges oriented to extend along the patient's teeth during use. The bite block may have a wall extending in the vertical plane and the alignment guides may two slots with one slot formed in each opposing side of that wall, with the two slots being parallel and extending rearward along a length of the wall. Further, each support arm may have a generally rectangular cross-section which forms part of the mating alignment guide and the alignment slots advantageously have a size and cross-sectional shape that mates with that rectangular cross-section. The above variations may be used alone or in each of the various combinations with each other.

There is also provided a method of administering an anesthetic to a mandible, wherein the location of the mandibular foramen is predetermined by measuring a plurality of mandibles on skulls to determine an average location of the mandibular foramen. An alignment guide is then provided on a bite block and a mating alignment guide is provided on a support plate. The support plate has a positioning stop located to abut the anterior border of the Ramus when the alignment guide and mating alignment guide are in mating engagement. A needle guide is connected to the support plate in a position and orientation relative to the support plate (preferably the position stop on the support plate) so the needle guide aligns with the predetermined location of the mandibular foramen when the position stop abuts the anterior border of the Ramus while the support plate is connected to the bite block. Advantageously, the method includes a tongue depressor along a length of the needle guide, and may further include a short ledge or flange around part of the tongue depressor to help keep the tongue off of the tongue depressor. This method further allows a dentist to use the alignment guide to guide a needle of a syringe of anesthetic to the predetermined location of the mandibular foramen. The support plate may be removed while the bite block may be removed and/or reinserted for use during the dental procedure for which the anesthetic was administered. After use, the support plate and bite block may be autoclaved before reuse.

BRIEF DESCRIPTION OF THE DRAWINGS

These and other features and advantages of the invention will become more apparent in light of the following discussion and drawings, in which like numbers refer to like parts throughout, and in which:

FIG. 4 is a top, perspective view of the support plate and needle guide;

FIG. 5 is a bottom perspective view of the support plate and needle guide;

FIG. 6 is a bottom view of the support plate and needle guide;

FIG. 7 is a top view of the support plate and needle guide of FIG. 6;

FIG. 8 is a right-side view of the support plate and needle guide of FIG. 7;

FIG. 9 is a left side view of the support plate and needle guide of FIG. 9;

FIG. 10 is a back-side view of the support plate and needle guide of FIG. 7;

FIG. 15 is a left side view of the bite block of FIG. 13 showing the front of the bite block;

FIG. 16 is a top view of the bite block of FIG. 13 sowing the top of the bite block;

FIG. 17 is a top view of a support plate on a mandible in a use position taken parallel to the Z axis and showing the X-Y plane;

DETAILED DESCRIPTION

Figure 1:
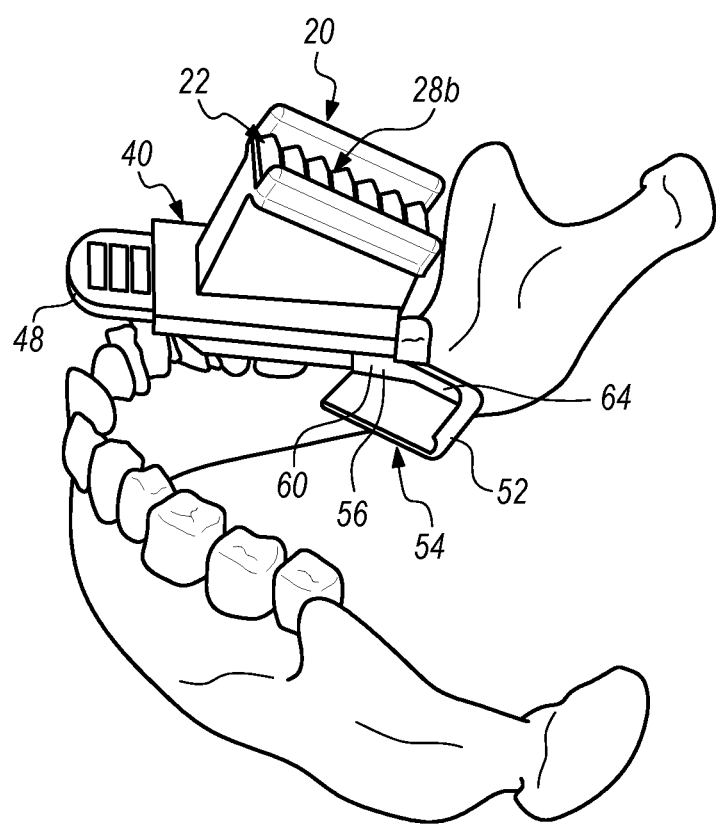
FIG. 1 is a perspective view of a mandible with a bite block, support plate and needle guide on the mandible.
Figure 2:
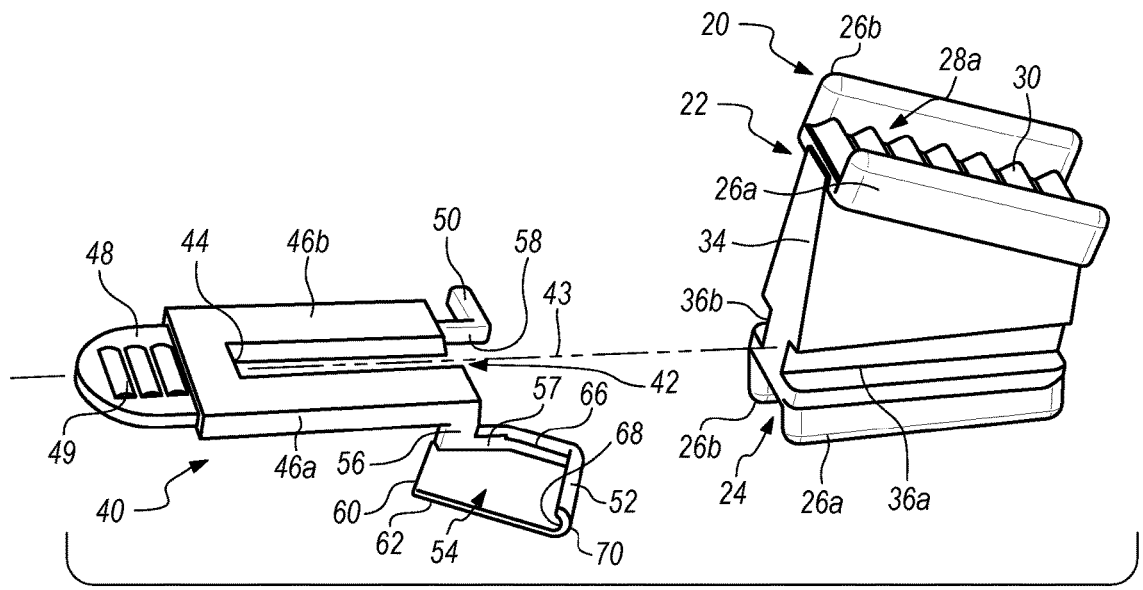
FIG. 2 is an upper, exploded perspective view of the bite block, support plate and needle guide of FIG. 1 but in an unassembled configuration.
Figure 3:
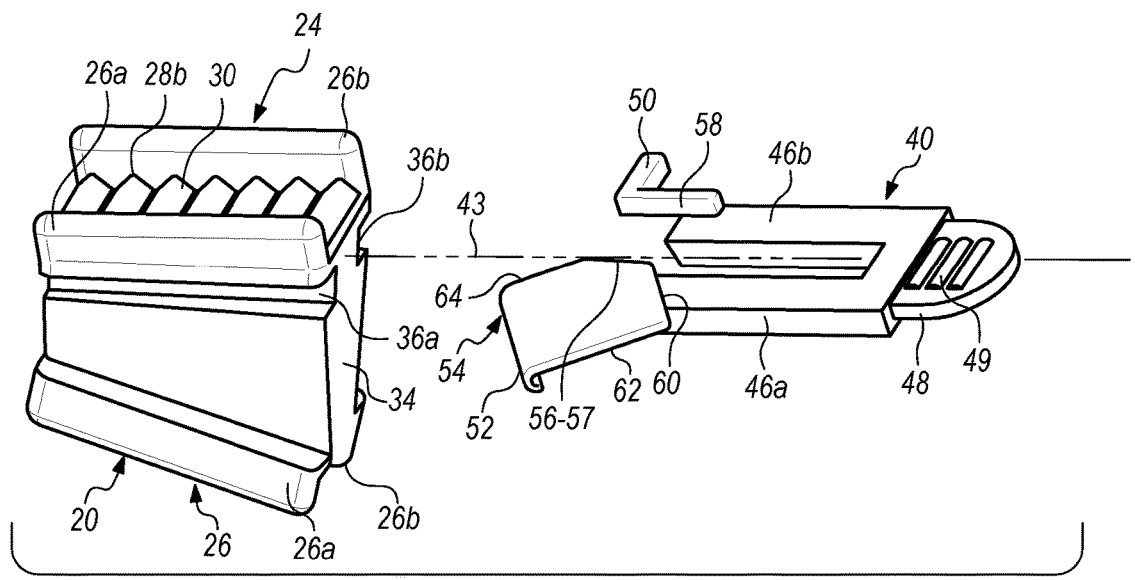
FIG. 3 is a bottom, exploded perspective view of the bite block, support plate and needle guide of FIG. 2.
Figure 11:
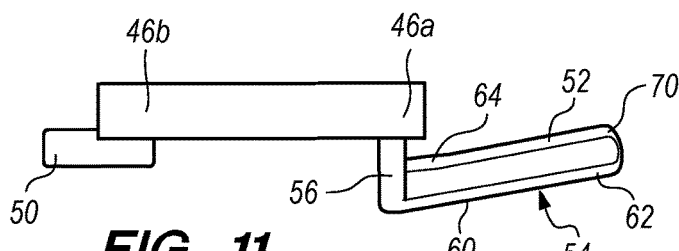
FIG. 11 is a front side view of the support plate and needle guide of FIG. 7.
Figure 12:
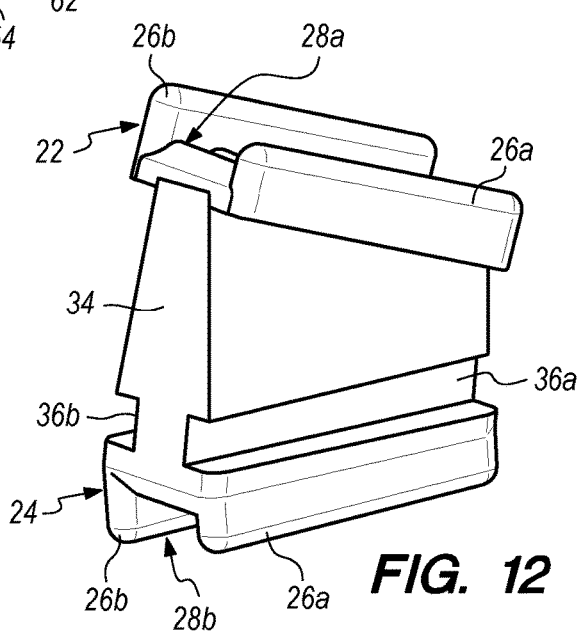
FIG. 12 is a front perspective view of the bite block of FIG. 1.
Figure 13:
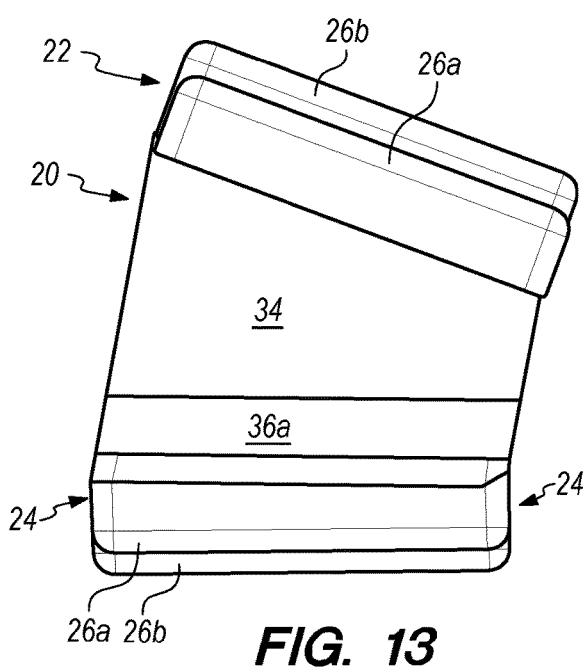
FIG. 13 is a side view of the bite block of FIG. 12.
Figure 14:
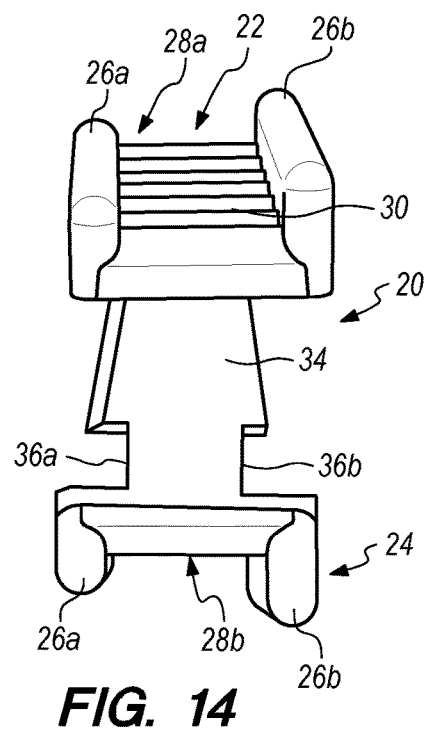
FIG. 14 is a right-side view of the bite block of FIG. 13 showing the back of the bite block.

As used herein, the relative directions and terms inner and outer, inward and outward, anterior and posterior, are with respect to the sagittal plane. The relative terms front and rear, forward and backwards and behind, ventral and dorsal, anterior and posterior are relative to directions parallel to the sagittal plane with the back direction being toward a person's throat, and front being the opposite direction toward a person's front teeth when viewed from the back of the person's throat. The relative directions and terms upper and lower, top and bottom, above and below are with respect to the relative directions corresponding to the upper and lower teeth in a person's mouth or oral cavity, where the lower teeth are on the person's mandible, and also correspond to the vertical axis when a person's mandible is horizontal. The relative directions and terms inner and outer, inward and outward are with respect to the patient's mouth, with inner being inside the patient's mouth and the outer or outward direction being toward the patient's cheek. These relative inner and outer directions and locations may be lateral, along an axis perpendicular to the sagittal plane, or along an axis oriented at an angle to that sagittal plane. Thus, an inner side of the teeth may abut the patient's tongue while an outer side of the teeth may abut the patient's cheek or lips.

As used herein, the "occlusal plane" refers to an imaginary surface touching the occlusal or biting surfaces of the teeth, including the incisors and posterior or occlusal teeth. It represents an average.

As used herein, the following part numbers refer to the following parts: 20—bite block; 22—upper tooth engaging portion; 24—lower teeth engaging portion; 26*a*—inner side flange; 26*b*—outer side flange; 28*a*, 28*b*—upper and lower teeth engaging surface; 30—ridges; 34—wall; 36*a,b*—alignment slots; 40—support plate; 42—slot; 43—slot axis; 44—slot end; 46*a,b*—inner and outer support arms; 48—handle; 49—lateral ridges on handle; 50—position top; 52—needle guide; 54—tongue depressor; 56—first adjustment arm; 57—leg of adjustment arm; 58—second adjustment arm; 60—front side of tongue depressor; 62—inner side of tongue depressor; 64—outer side of tongue depressor; 66—second tongue depressor flange; 68—needle opening; 70—corner opposite truncated corner; 74—needle tip; 76—syringe; and 78—needle tip.

Referring to FIGS. 1-3 and 12-16, a bite block 20 has upper and lower teeth engaging portions 22, 24, respectively, located to engage respective upper and lower teeth on a patient's upper and lower jaws. The tooth engaging portions 22, 24 advantageously have at least one side flange 28 and preferably has opposing inner and outer side flanges 26a, 26b, respectively, which extend along a portion of the upper and lower teeth, respectively, during use. The tooth engaging portions 22, 24 advantageously have a U-shaped cross-section with two side flanges 26a, 26b. Advantageously, the outer side flange 26b is longer than the inner side flange 26a, with neither side flange long enough to abut the patient's gums during use. A short side flange 26a of about 3 mm and a side flange 26b of about twice as high, about 5 mm is believed suitable. The side flanges 26a, 26b are located on opposing sides of the teeth during use and help keep the bite block from rotating about a vertical axis through the teeth during use. The longer or higher flange is advantageously on the outside of the teeth, abutting or adjacent to the patient's cheek.

Between the side flanges 26a, 26b is a tooth engaging surface 28, which is denoted by part 28a for the upper tooth engaging surface and 28b for the lower teeth engaging surface 28b. The tooth engaging surfaces 28a, 38b advantageously has a textured surface to better engage and grip the patient's teeth during use. Advantageously, the texture comprises a plurality of parallel ridges 30 extending between opposing side flanges 26a, 26b, with the ridges 30. Ridges 30 with opposing inclined sides forming a generally triangular cross-section at the ridges are believed suitable. As the tips of the ridges 30 abut the patient's teeth during use, the tips define the tooth engaging surfaces 28a, 28b.

The upper and lower teeth engaging portions 22, 24 are inclined relative to each other during use, with the teeth engaging portions inclined toward an intersection adjacent the juncture of the patient's jaws. Some bite blocks use resilient V-shaped bite blocks with the teeth engaging portions along each side of the V when the V-shaped bite block is generally horizontal. It is believed advantageous to have the teeth engaging portions 22, 24 joined by a wall 34 that is generally vertical during use. The wall 34 is shown as having a generally triangular cross-sectional shape narrower at the top and wider at the bottom formed by slightly inclined opposing sidewalls, but the opposing side walls may be parallel for a wall 34 of generally uniform thickness. The inclination angle is not believed critical and may be varied to accommodate the user's jaw and teeth. Teeth engaging portions 22, 24 inclined at an angle of about 20° are believed suitable. Although larger inclination angles of 21-40° are believed usable they become increasingly uncomfortable for the patient as the inclination angle increases. Smaller angles of inclination of 12-19° are also believed suitable but the smaller inclination angle reduces the working space in the oral cavity during use and does not stabilize relative movement of the upper and lower jaws as well as larger inclination angles of the teeth engaging portions.

Inner and outer alignment guides, shown as alignment slots 36a, 36b are formed on opposing inner and outer sides, respectively, of the wall 34. The alignment slots 36a, 36b are advantageously adjacent to the lower teeth engaging portion 24 and are advantageously parallel with the lower teeth engaging surface 28b. The alignment slots 36a, 36b are advantageously directly opposite each other with the space between the slots 36 being about the same as the thickness of the wall 34 adjacent the upper tooth engaging portion 22. Thus, the wider base formed by the inclined sidewalls of wall 34 of the generally triangular wall 34 accommodate the depth of the alignment slots 36a, 36b while avoiding a significant weakening of the wall 34. This results in the lower surface of the alignment slots 36a, 36b extending slightly further away from a center plane of the wall 34 than the upper surface of the slots, so that the upper surface of the sideways facing or laterally facing alignment slots 36 is shorter than the lower surface of those alignment slots. The alignment slots 36a, 36b advantageously extend along the entire length of the wall 34 and bit block 20, but need not do so. The inner and outer alignment slots 36a, 36b are advantageously in the same vertical plane as the inner and outer flanges 26a, 26b during use, with the wall 34 being in the same vertical plane as the upper and lower engaging surfaces 28a, 28b.

Referring to FIGS. 1-11, a support plate 40 advantageously has a generally rectangular body. A closed-ended slot 42 having closed end 44, forms inner and outer support arms 44a, 44b, respectively, on opposing sides of the slot 42, so the arms define the slot. The slot 42 extends along axis 43 with the slot opening onto a back of the support plate 40, with the closed end of the slot adjacent the front end of the support plate. The support plate 40 has an optional manipulating tab or handle 48 at its front end. Advantageously, the handle 48 may be textured to make it easier to grip and manipulate without slipping. Lateral ridges 49 aligned generally perpendicular to the axis of the slot 42 are to help ensure secure gripping by the fingers of the dentist.

The support plate 40 has two mating alignment guides configured to mate with the alignment guides (e.g., alignment slots 36) on the bite block to align and guide the support plate relative to the bite block as the support plate moves relative to the guide block. The mating alignment guides are depicted as two, spaced apart and parallel, inner and outer support arms 46a, 46b, respectively.

A position stop 50 is connected to the outer support arm 46b while a needle guide 52 and tongue depressor 54 are connected to the inner support arm 46a, so the relative locations and orientations of the position stop 50 and the needle guide and tongue depressor 54 are predetermined by the construction of the support plate. A first (inner) adjustment arm 56 helps locate the tongue depressor 54 relative to the inner support arm 46a while a second (outer) adjustment arm 58 helps locate the position stop 50 relative to the outer support arm 46b. The bottom of the position stop 50 is advantageously generally parallel with and preferably in the same plane as the lower teeth engaging surface 28b so the bottom of the position stop lies in or close to the occlusal plane.

During use, the rearward facing, closed slot end 44 can contact the front end of the wall 34 to limit the maximum insertion position of the support plate 40 relative to the bite block 20 and thus limit the maximum insertion position of the needle guide 52 and tongue depressor 54 relative to the bite block. Likewise, contact of the position stop 50 with the anterior border of the Ramus of the mandible will position the tongue depressor 54 and needle guide 52 relative to the bite block 20, and position the needle guide and tongue depressor relative to the mandible, the teeth of which abut the lower engaging surface 30 and lower teeth guide 24 of the bite block 20.

The alignment guides on the bite block engage the mating alignment guides on the support plate for relative movement between the parts. Thus, the inner and outer support arms 46a, 46b are sized to snugly fit into the respective inner and outer alignment slots 36a, 36b. In the depicted embodiment the alignment slots 36a, 36b are generally rectangular in cross-section and the support arms 46a, 46b are generally rectangular in cross-section. Advantageously the back ends of the support arms 46a, 46b are rounded or tapered or inclined to make it easier to align and insert the inner and outer support arms 46a, 46b into the corresponding mating alignment slots 36a, 36b. In the depicted embodiment the inside ends of each support arm 46a, 46b are slightly inclined downward to form an inclined surface to more easily fit into the front end of the corresponding and mating alignment slot 36a, 36b. The fit between the alignment slots 36 and support arms 46 is advantageously sufficient to allow the support plate 40 to be slid along the length of the alignment slots 36 by manual manipulation of the handle 48 and support plate 40 connected to the handle. The support arms 46, 46b are spaced far enough apart laterally in the traverse plane, and the fit is sufficiently tight to reduce rotation of the support arms 46 and support plate 40 about axis 42 to a few degrees, and preferably to less than about one degree so as to more accurately position the needle guide 52 relative to the bite block 20 and relative to the desired location on the patient's mandible. Moreover, the length of the support arms 46 and mating alignment slots 36 are sufficient to avoid rocking or rotation of those parts relative to each other about an axis perpendicular to axis 43 so any rotation is less than a few degrees and preferably less than about one degree.

The positioning stop 50 extends outward, preferably laterally in a transverse plane generally parallel to axis 43 of slot 42 and is located to abut the anterior border of the Ramus. To reach that location in the illustrated embodiment, the outer adjustment arm 58 extends the positioning stop 50 downward to a location below the bottom of the outer support arm 46b, and extends the positioning stop back, behind the end of that outer support arm. During use, the positioning stop 50 abuts the anterior border of a ramus, or more accurately the flesh enclosing the anterior border of a ramus, adjacent the rear molar of the mandible. If the support arms 46 are too long they can make the patient uncomfortable or the inner support arm can induce gagging. Thus, the support arms 46a, 46b are preferably about the same length as the alignment slots 36a, 36b and the slot end 44 acts as a limit stop to prevent the rear end of the inner support arm and/or parts connected thereto from extending far enough to cause gagging. But the desired position of the position stop 50 and the needle guide 52 advantageously occur before the slot end 44 hits the wall 34 to stop backward movement of the support plate, position stop and needle guide.

The second adjustment arm 58 connects the position stop 50 to the back end of the outer support arm 46b. The second adjustment arm 58 connects to the lower surface of the outer support arm 46b, at the back end of that support arm. The second adjustment arm 58 extends along the outer side flange 26b during use, but further back into the mouth along the mandible. Because the position stop 50 extends laterally, the second adjustment arm 58 extends generally parallel to the outer support arm 46b, along the outer side of the patient's mandible during use, and advantageously connects to the inner end of the position stop 50. The second adjustment arm 58 is advantageously smaller in cross section than the support arm 46b. The second adjustment arm 58 and position stop 50 advantageously form an L-shaped part with the position stop 50 forming the short, outward extending leg of the L-shaped part and having a generally square, cross-sectional shape about 2 mm×2 mm, with rounded corners. The long leg of the L-shaped part formed by the second adjustment arm 58 has a generally rectangular cross-sectional shape about 1 mm×2 mm and extends behind the back end of the outer support arm 46b a distance of about 10 mm. During use, the position stop 50 is on the outer side of the patient's teeth and gums and extends beyond the back end of the bite block and its outer side flange 26b, so the bottom of the position stop 50 is in the plane containing along the top of the patient's molars, and advantageously parallel to and preferably in the same plane as the lower teeth engaging surface 28b.

The tongue depressor 54 is inside the patient's lower jaw during use but close to the mandible. The tongue depressor 54 has a complex shape and orientation that may perform several functions described in more detail later. The described tongue depressor 54 is connected to the first adjustment arm 56 and is located below the lower side and back end of the inner support arm 46a. The first adjustment arm 56 extends downward along the inner side of the patient's teeth during use, may extend along the inner side flange 26a of the bite block 20. The first (inner) adjustment arm 56 may have an L-shape with the first adjustment arm 56 forming the vertical part of the L-shape and a short leg 57 of the L-shape extending back, further into the mouth toward the patient's throat. The tongue depressor 54 may be connected to this first adjustment arm 56 and/or short leg 57.

The tongue depressor 54 has a generally square shape but has one truncated corner so it actually has five sides—one of which extends across the truncated corner. The short-leg of the L-shaped first adjustment arm 56 extends along this truncated corner of the tongue depressor 54 and forms an upward-extending flange on the top side of the tongue depressor. The upwardly extending flange formed by the lower end of the first adjustment arm 56 and/or the short leg 57 of that first adjustment arm—forms a first tongue depressor flange that for convenience is referred to as first tongue depressor flange 56-57, which extends along the truncated corner.

The remaining four sides of the generally square tongue depressor 54 complete the generally square shape of the tongue depressor 54. Front side 60 is generally parallel to and opposite the back side along which needle guide 52 extends. Inward facing side 62 joins the inner end of the needle guide 52 and joins the front side 60. The needle guide 52 extends along the back of the generally square tongue depressor. The generally square tongue depressor is canted so the intersection of inner side 62 and the needle guide 52 is toward the middle of the tongue depressor during use and generally opposite the first tongue depressor flanges 56-57. The tongue depressor 54 has outer side 64 that is generally parallel to inner side 62 and joins the outer end of needle guide 52 with the truncated corner extending along flange 56 and 57. The outer side 64 is perpendicular to the needle axis extending along the needle guide 52 and allows passage of a needle extending along that needle axis and needle guide. As noted, the depicted tongue depressor 54 may have five sides, as one corner of the plate is truncated by a side and flange 56-57 extending at an angle of about 65° relative to the sagittal plane, during use. The angle allows the side flange 56-57 and associated tongue depressor to extend generally parallel to the axis 43 and extend along the inside of the patient's adjacent mandible as aligned by the support plate 40 mating with the bite block's alignment slots 36.

A second tongue depressor flange 66 advantageously extends upward along the outer side 64 on the upper surface of the tongue depressor 64. The inner support flange 66 has one end connected to the back end of the first tongue depressor flange 56 and 57, and has its other end connected to or ending adjacent to the juncture with the back, outer end of the needle guide 52, with needle opening 68 located at that juncture and preferably formed in that flange 66.

The first tongue depressor flange 56 and 57 forming the truncated corner of the tongue depressor 52, is slightly inclined downward and further inclined toward the back of the patient's throat. As the generally rectangular plate is preferably planar, the second tongue depressor flange 66 extends slightly downward. The second tongue depressor flange 66 also extends inward toward the sagittal plane and backward toward the patient's throat. The flanges 56, 57 and 66 are on the outer side of the tongue depressor and press against the outer side of the patient's tongue in use. Those flanges provide a broader surface than the edge of the generally flat plate formed by the remainder of the tongue depressor and help avoid discomfort in urging the tongue away from the mandible and needle that administers the anesthetic shot.

The corner 70 of the tongue depressor 54 opposite the truncated corner of the tongue depressor is the highest corner of the tongue depressor, while the needle opening 68 at the end of the needle guide is the lowest corner of the tongue depressor. The needle guide 52 extends along a downwardly and outwardly inclined needle axis that should be aligned with the predetermined anesthetic injection location when the support plate 40 and bite block 20 are properly positioned with the position stop 50 against the anterior border of the Ramus.

The needle guide 52 extends along an axis defined by a downwardly, outwardly and slightly rearwardly extending flange along the back edge of the tongue depressor 54. The needle guide 52 preferably forms a curved wall having a C-shaped cross-section curved with an inner diameter about 2-4 times the diameter of the tip of the needle 74 of the syringe 76 used to inject an anesthetic. The axis of curvature of the curved wall of needle guide 52 is advantageously shaped to allow a needle to abut against the curved flange forming the needle guide 52, and if moved along that flange allow the needle tip 78 to penetrate the jaw soft tissue and administer anesthetic at the location where the inferior alveolar nerve is believed to enter the mandible, at the mandibular foramen. A straight flange at an acute angle or right-angle bend may be used instead of the curved flange 52.

Referring to FIGS. 1-3 and 17-18, the needle guide and the needle opening 68 are advantageously aligned along an axis which intersects the location on the patient's jaw where the inferior alveolar nerve enters the mandible, at the mandibular foramen. That location where the nerve enters the mandible was measured relative to the occlusal plane and the anterior border of the Ramus of the mandible and averaged over several mandibles based on measurements of skulls from skeletons. The bottom of the position stop 50 is advantageously located to abut the anterior border of the Ramus at the occlusal plane, preferably at the outer side of the mandible. The needle guide 52 was then connected to the support plate and oriented to intersect that desired location on the mandible where the alveolar nerve enters the mandible, namely, at the mandibular foramen on either the right or left side of the mandible. The location of the mandibular foramen for adults has been determined by measurement and averaging of skeletal mandibles and is discussed later.

In use, the bite block 20 establishes a stationary base in the oral cavity that is aligned in a known general position relative to the patient's teeth and upper and lower jaws. The support plate 40 moves relative to the bite block 20 to position the needle guide 52 and tongue depressor forward and backward relative to the bite block and along a predetermined axis of the bite block and the patient's teeth and jaws. The position stop 50 abuts the anterior border of the Ramen and the desired injection location on the inside of the mandible is known relative to that location of the position stop 50. Thus, the position stop 50 can position the sliding plate 40, needle guide 52 and tongue depressor 54 at a desired location along the bite block's predetermined axis relative to then patient's mandible. The needle guide 52 positions the needle guide so an axis extending along the needle guide intersects the desired location on the inside of the mandible for administering the anesthetic when the position stop 50 positions the support plate and needle guide 52 relative to the user's mandible. The tongue depressor 54 moves or urges the tongue out of the way of the needle's path when the positioning stop 50 aligns the needle guide 52 with respect to the patient's jaw, with the tongue depressor's orientation selected to reduce and avoid gagging.

In more detail, during use, an appropriate bite block 20 is selected for use, depending on the bite block construction and whether the anesthetic is to be administered on the left or right side of the patient's mandible. Because of the inner and outer side flanges 26a, 26b and the alignment slots 46, the same bite block 20 may not be simply moved from the left mandible to the right mandible. Thus, a separate left and right bite block are preferably used if the flanges 26a, 26b and alignment slots are used. If the side flanges 26a, 26b are not used and the alignment mechanism is suitable for use on either side of the mouth, then a single bite block may be possible for use on both sides of the mouth for aligning the support plate and needle guide on either side of the mouth. As the position stop 50, tongue depressor 54 and needle guide 52 are orientation dependent, a left and right support plate 40, each the mirror image of the other, may be provided, with the appropriate one selected depending on which side of the mouth the anesthetic is administered.

The appropriate bite block 20 is placed on the side of the patient's mouth where the anesthetic is to be administered and urged toward the back of the patient's jaw, preferably a distance sufficient that the patient cannot easily open the jaws and dislodge the bite block, but not far enough to cause pain or injury. The patient's teeth abutting the opposing sides of the bite block 20 hold the bite block in place relative to the patient's mandible and teeth, with the engaging portions 22, 24, inner and outer side flanges 26a, 26b and tooth engaging surfaces 28a, 28b side flanges further helping to assure stability of the bite block relative to the patient's teeth and jaws. The side flanges 26 also help deter the patient from moving the upper and lower jaws laterally relative to each other as doing so may wedge the teeth against the flanges.

The precise location of the bite block 20 along the lower teeth and mandible is not believed critical as the bite block provides a stable base to allow more precise positioning of the support plate 40 and its needle guide 52 relative to the bite block. Thus, within a range of locations along the patient's lower teeth and mandible, a stable position of the bite block 20 is believed more important than a precise location on the teeth and mandible. The position of the support plate 40 relative to the bite block 20 determines the position of the needle guide and the needle alignment for administering the anesthetic and that position is determined by the position stop 50.

After the bite block 20 is positioned between the upper and lower teeth and the upper and lower jaws, the two support arms 46a, 46b of the appropriate left or right-side support plate 40 are inserted into the respective and mating alignment slots 36a, 36b. The alignment slots 36 are advantageously generally parallel to the axis 43 and a plane along the top of the patient's teeth to make insertion and removal of the support plate easier. But different inclinations of the alignment slots 36 may be used, in which case the orientation of the tongue depressor and needle guide may change, and the construction of the support plate will also change. The support plate 40 slides along the alignment slots 36 of the bite block until the position stop 50 hits the anterior border of the patient's Ramus, adjacent to but in back of the rear molar. The position stop 50 positions the support plate 40 and needle guide 52 relative to the bite block and to the patient jaw, with the handle 48 helping to insert the support plate and position stop. Advantageously, the dentist manually presses on the handle 48 to gently urge the position stop 50 against the flesh at the anterior border of the Ramus as the anesthetic is administered. In the described configuration, the support plate 40 positions the needle guide 52 along a length of the bite block so the needle guide is inclined downward, rearward and outward so the needle guide 52 extends along an axis intersecting a predetermined location which is believed to be the mandibular foramen.

The slot end 44 limits the distance the support plate and tongue depressor may be inserted into the patient's mouth, as inserting the tongue depressor too far can cause gagging. The tongue depressor 54 and needle guide 52 are inclined rearwardly and downwardly because if those parts were not so inclined and the needle guide aligned more closely to the desired injection location, then it is believed they would cause gagging in at least some patients by placing the back of the tongue depressor too far into the back of the patient's throat, and too far downward into the patient's tongue to depress the tongue comfortably while avoiding gaging.

When the needle guide 52 is correctly positioned by the position stop 50 and the support plate 40 and bite block 20, the dentist places the needle tip along the needle guide 52 and moves the needle tip 78 along the needle guide toward and through the needle opening 68. The needle guide 52 and flanges formed by the adjustment arms 56-57 and 58 help avoid inadvertent poking of the tongue with the needle tip 78. The needle tip is then passed along the needle guide 52, through the needle hole 68 and into the flesh of the mandible until the needle tip hits the mandible at which point the needle is withdraws slightly (a mm or so or even less) and the anesthetic is then administered, as for example, by manually squeezing the plunger of the syringe 76. The anesthetic is thus administered immediately adjacent the mandible. As used herein, immediately adjacent refers to a positive distance of about 1.5 mm or less. The position stop 50 is manually urged against the anterior border of the Ramus as the needle tip 78 is inserted and the anesthetic administered and the needle tip is removed from the patient's lower jaw and from the needle guide 52 and ultimately removed from the patient's oral cavity. As the needle tip is urged toward and against the mandible the nerves are sheathed in sufficient fatty tissue that they move out of the way of the needle tip so the tip can contact the bone and do not contact the needle tip.

Advantageously, the needle tip 78 is bent sideways about 90° to the longitudinal axis of the needle body. Bending the needle tip 78 avoids trying to distort the patient's mouth to allow the syringe to place needle tip 78 in an aligned position with the needle guide 52. It is advantageous to have the needle tip 78 abut the needle guide 52 along the length of the needle tip as the needle is slid through the needle opening 68. As the needle opening 68 is believed to be positioned within about 20-30 mm (about 0.8 to 1.2 inches) of the mandibular foramen where the nerves enter the mandible, any bend in the needle must allow enough length distal of the bend to reach the mandibular foramen, thus bending the needle about 40-50 mm (about 1.5 to 2 inches) below the end of the needle is believed suitable in order to allow for variations in the thickness of the soft tissue on the mandible. Manually bending the needle is believed suitable. Bending the needle at about 90° is believed desirable as it makes alignment easier, but bending the needle at obtuse angles between 179° and 91° is believed suitable, with angles between 120° and 135° also believed advantageous. Bending the needle tip at acute angles less than 90 is believed undesirable, in part because it is likely to restrict fluid flow through the bent needle and in part as it is believed to make alignment of the needle tip and the needle guide more difficult.

The needle tip 78 is then withdrawn after administering the anesthetic. The support plate 40 may also be withdrawn from the bite block 20 and the bite block also optionally removed to allow the patient to relax the jaw while the anesthetic takes effect. The bite block 20 may optionally be reinserted into the oral cavity if used in the following dental procedures after the anesthetic takes effect if the dentist wants to use it to maintain the upper and lower jaws separated. After administering the anesthetic and being removed from the patient's oral cavity, the support plate 40 and dental block 20 may be either discarded, or advantageously, autoclaved at a temperature sufficient to destroy any bacteria, germs or viruses or all of them.

A bite block 20 having inclined tooth engaging portions 22, 24 in fixed position relative to each other is preferred. But if the alignment slots 36a, 36b are formed in a portion of the bite block 20 that does not move once the bite block is positioned, the upper tooth engaging portion 24 or tooth engaging surface 28a, may be allowed to move relative to the lower teeth engaging portion and lower teeth engaging surface 28b and a vertically truncated wall 34.

The lower teeth engaging portion 24 and lower teeth engaging surface 28b may have a length of about 30 mm (about 1 and ⅛ inches) and advantageously extend across 2-3 teeth, preferably including molars and bicuspids. The support plate 40 is advantageously aligned with the occlusal plane during use and a shorter length bite block 20 and tooth engaging portion 24 allows the user more flexibility in positioning the bite block in the patient's mouth during use while still aligning the support plate with the occlusal plane.

The alignment guides are depicted as including alignment slots 36a, 36b that are shown as located in the same general plane but may be in vertically offset planes as long as the location of support arms 46a, 46b are located to correspond with the slots 36. Further, the alignment slots 36 and mating support arms 46 are shown as having a generally rectangular cross-section but other cross-sectional shapes may be used, including triangular, curved, circular, or polygonal cross-sectional configurations.

The bite block 20 is shown using slots 36a, 36b to align the support plate relative to the bite block. But instead of alignment guides comprising female recesses or receptacles (e.g., slots 36) in the bite block 20 mating with male protrusions (e.g., arms 46) on the support plate 40, the bite block could have male protrusions and the support plate could have female receptacles or recesses. Thus, the alignment guides on the bite block 20 could comprise male protrusions such as ledges or flanges that extend outward from opposing edges of the bite block 20 and the support plate 40 could have recesses configured to mate with the flanges or ledges or other male protrusions. The protrusions could have cross-sections with sharp corners such as square, rectangular, triangular or other polygon cross-sections. The protrusions could have curved cross-sections such as generally circular or semi-circular or elliptical or oval cross-sections. In the above variations of the alignment guides (e.g., alignment slots 36) and mating alignment guides (e.g., support arms 46), the cross-sectional shape and location of the mating male and female parts of the bite block 20 and support plate 40 advantageously have mating shapes so the support plate is aligned with and guided along a length of the bite block to locate the position stop 50 at the anterior border of the Ramus and position and orient the needle guide 52 to align along an axis with the mandibular foramen. Additionally, while the male engaging portion such as arms 46 are shown as continuous, they could be discontinuous or intermittent—but preferably still provide sufficient engagement to provide a stable and consistently positioned needle guide. Further, while the alignment slots 36 are adjacent the lower teeth engaging portion 24 they need not be so located as the location of the support stop and needle guide could be altered to compensate for relative positional changes of the parts. Thus, while alignment guides may comprise rectangular cross-section support arms 46a, 46b and mating alignment guides have rectangular cross-section alignment slots 36a, 36b extending along and parallel to the lower teeth engaging portion 24 and lower teeth engaging surface 28b, the alignment guides and mating alignment guides are not so limited in shape or location or operation.

The position stop 50 is described as hitting the anterior border of the Ramus at the occlusal plane, preferably at the outer side of the mandible. But as long as the position stop 50 hits the anterior border of the Ramus at a known location relative to the predetermined location of the mandibular foramen the location and orientation of the needle guide 52 and optional tongue depressor 54 may be adjusted as appropriate. Relative locations of the position stop 50, needle guide 52 and tongue depressor 54, and of the support arms 46a. 46b to which those parts are connected, are preferably limited so as not to cause the patient to gag or experience discomfort during use.

The predetermined location of the mandibular foramen was calculated based on an average of mandibles on skulls, relative to the occlusal plane and the anterior border of the Ramus, at the outer or lateral side of the mandible. Referring to FIGS. 1 and 17-19, the relative dimensions and locations are given for the illustrated parts on a mandible, with the 0, 0, 0, origin of an X, Y, Z coordinate system located at the bottom of the position stop 50 as it abuts the anterior border of the Ramus in the occlusal plane, on the outer side of the mandible. For the right side of the mandible, that predetermined location of the mandibular foramen is believed to be at about 0.0, 15.4, −8.9 mm, where XY is the transverse plane, XZ is the sagittal plane, and YZ is the coronal plane. For the left side of the mandible, that predetermined location is believed to be the mirror image at 0.0, −15.4 and −8.9 mm relative to the location where the bottom of the position stop 50 abuts the anterior border of the Ramus at the occlusal plane of the right mandible (with the "right" side as viewed from the perspective of the patient).

Figure 18:
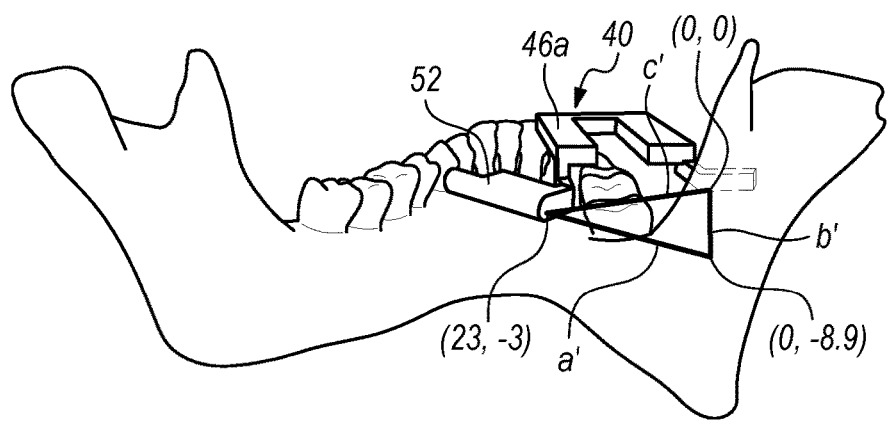
FIG. 18 is a view of the support plate and mandible of FIG. 17, taken parallel to the Y axis and showing the X-Z plane.
Figure 19:
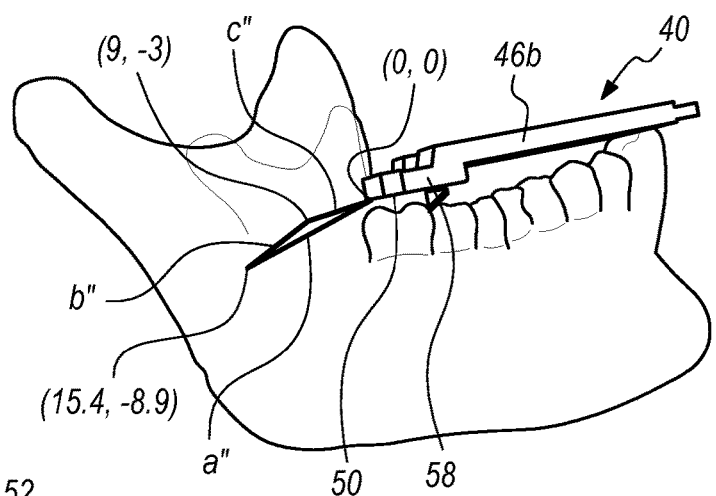
FIG. 19 is a view of the support plate and mandible of FIG. 17, taken along the X axis and showing the YZ plane.
Figure 20:
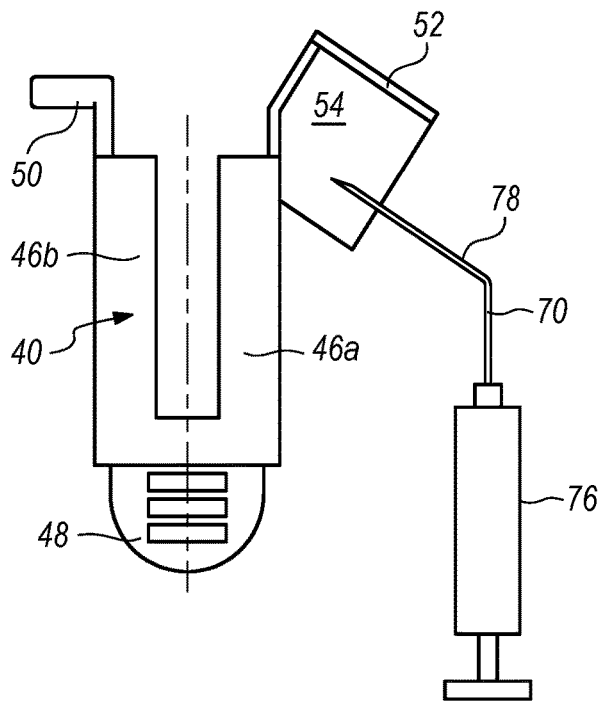
FIG. 20 is a plan view showing a syringe with a needle tip for use with a needle guide on a support plate.

The location and orientation of the needle guide 52 is fixed by the position stop 50 as they are both parts of the same support plate that is a sufficiently stiff part that the relative positions of the position stop on and needle guide 50 do not change during use by an amount sufficient to degrade acceptable performance of the apparatus for aligning needles to administer anesthetic to the predetermined location of the mandibular foramen. Referring to FIGS. 17-19, the relative distances and angles of the needle guide 52 relative to the position stop 50 and the predetermined location of the mandibular foramen are given for the illustrated configuration, with the origin of the X, Y, Z axes located as stated immediately above.

In the X-Y plane shown in FIG. 17, the distance a from the opening 63 to the predetermined location of the mandibular foramen is 23.9 mm, the distance b from the predetermined location of the mandibular foramen to the location where the bottom of the position stop 50 abuts the anterior border of the Ramus is 15.4 mm and the distance c from the location where the bottom of the position stop 50 abuts the anterior border of the Ramus to the needle opening 68 is 24.7 mm. The angle between distances ab is 74.4°, the angle between distances bc is 68.7°, and the angle between distances ac is 36.9°—as viewed in the X-Y plane. In the X-Y plane the coordinates in millimeters for the predetermined location of the mandibular foramen are (0, 15.4), the coordinates for the opening 68 are (23, 9), and the bottom of the position stop 50 at the anterior border of the Ramus in the occlusal plane at the outer side of the mandible is (0,0).

In the X-Z plane shown in FIG. 18, the distance a' from the opening 63 to the predetermined location of the mandibular foramen is 23.7 mm, the distance b' from the predetermined location of the mandibular foramen to the location where the bottom of the position stop 50 abuts the anterior border of the Ramus is 8.9 mm and the distance c' from the location where the bottom of the position stop 50 abuts the anterior border of the Ramus to the needle opening 68 is 23.2 mm. The angle between distances a'b' is 75.9°, the angle between distances b'c' is 82.3°, and the angle between distances a'c' is 21.8°—as viewed in the X-Z plane. In the X-Z plane the coordinates in millimeters for the predetermined location of the mandibular foramen are (0, 8.9), the coordinates for the opening 68 are (23, −3), and the bottom of the position stop 50 at the anterior border of the Ramus in the occlusal plane at the outer side of the mandible is (0,0).

In the Y-Z plane shown in FIG. 19, the distance a" from the opening 63 to the predetermined location of the mandibular foramen is 17.8 mm, the distance b" from the predetermined location of the mandibular foramen to the location where the bottom of the position stop 50 abuts the anterior border of the Ramus is 8.7 mm and the distance c" from the location where the bottom of the position stop 50 abuts the anterior border of the Ramus to the needle opening 68 is 9.5 mm. The angle between distances a"b" is 12.6°, the angle between distances b"c" is 155.9°, and the angle between distances a"c" is 11.5°—as viewed in the Y-Z plane. In the Y-Z plane the coordinates in millimeters for the predetermined location of the mandibular foramen are (9, −3), the coordinates for the opening 68 are (15.4, −8.9), and the bottom of the position stop at the anterior border of the Ramus in the occlusal plane at the outer side of the mandible is (0,0).

The above dimensions are specified to fractions of a millimeter and fractions of a degree but the variation in human anatomy and musculature does not allow for such accurate location of the mandibular foramen relative to the above designated origin of the X, Y, Z coordinate system. Further, the predetermined location is based on averaged values, thus some variation in actual use exists. Accuracy to the extent implied by the above numerical values is fortunately not necessary, in part because the anesthetic needle is advances until it hits the bone and in part because the anesthetic is absorbed laterally through the tissue. Thus, while the method and apparatus described herein may not always align the needle axis with the mandibular foramen, it is believed to greatly improve results and provides consistent, reproducible results for the same patients, and across a variety of patients.

These various locations and orientations are believed to allow alignment of the needle tip 78 with the predetermined location of the mandibular foramen while allowing the tongue to be positioned by the tongue depressor 54 to avoid poking the tongue with the tip of the needle, and while avoiding gagging. Other locations of the opening for the needle guide 52 may be used and other angles of orientation may be used to align the axis of the needle guide and corresponding needle axis with the predetermined location of the mandibular foramen, with some locations and orientations being more prone to induce gagging or interfere with the tongue than other locations. Also, the above dimensions and angles are with respect to the location of the position stop 50 at a defined location on the Ramus of the mandible and other numerical values of position and angle will arise by altering the location of the position stop, or by changing the location and orientation of the needle guide 52 and/or tongue depressor 54.

The needle guide 52 is shown as a curved flange within which the needle tip 78 may be inserted and moved anywhere along the length of the needle guide. More tight control over the positioning may be achieved by extending the needle guide 52 closer to the tongue depressor 54 so the needle tip 78 must be inserted through the end of the needle guide and pass the entire length of the needle guide. The relative size of the interior entrance to the needle guide and the diameter of the needle are correlated to make it easy to insert the needle tip while maintaining the accuracy with which the needle is guided to the desired location on the mandible. Further, while a curved flange on the needle guide 52 is preferred, the needle guide may be formed with other shapes, including right angle bends or acute angle bends between the generally planar tongue depressor and the upward extending flange forming the needle guide.

The tongue depressor 54 is shown as having a generally rectangular shape with a truncated corner. But other shapes of the tongue depressor may be used to position the needle tip 78 and needle guide 52 and align the needle guide, while moving the patient's tongue out of the way and depressing the tongue to clear a path for the needle tip to reach the mandible. Moreover, while the tongue depressor 54 is preferably planar, other shapes may be used, including curved surfaces, with slightly upwardly or downwardly dished surfaces believed suitable, although connecting the tongue depressor to a straight needle guide may be more difficult.

The bite block 20 and support plate 40 are advantageously made of a polymer suitable for dental use. The bite block 20 and support plate 40 may be made of disposable material, but are preferably made of a material suitable for repeated autoclaving without cracking, while providing a sufficiently stiff and inflexible material that the positioning of the needle guide remains stable during use. Materials such as Dental SG resin (made by Formlabs), polypropylene or polycarbonate are believed suitable for use. The bite block 20 and support plate 40 may be injection molded, machined from a suitable material, or made with 3-D printing. The support plate 40, needle guide 52 and tongue depressor 54 are advantageously integrally formed of a single material to avoid inadvertent disconnection of the tongue depressor and needle guide in the patient's mouth as those parts may be small enough by themselves to swallow or induce choking. Thus, the connection of those parts to the support plate and the construction of those parts is sufficiently strong to avoid them from breaking off or becoming separated from the support plate during normal use. The bite block 20 and support plate 40 are advantageously separate but releasably connectable parts for ease of use and sanitary cleaning for re-use, but could be integrally formed or made of multiple parts connected together. As used herein, the term "rectangular" includes a square, and vice versa.

The depicted bite block 20 has a length of about 1.2 inches measured along the lower teeth engaging surface 28b and slightly shorter on the upper tooth engaging surface 28a. The vertical distance between the upper and lower teeth engaging surface 28a, 28b is about 1.15 inches at the large, outer end and about 0.8 inches at the smaller, inner or proximal end and those dimensions include the height of the ridges 30 which are about 0.1 inches for each ridge. The depicted support plate 40 has arms 46a, 46b about 0.1 inches thick and 0.3 inches wide and spaced apart about 0.3 inches to form a 0.3-inch-wide slot between the arms. Each arm 46a, 46b has a length of about 1.4 inches on the bottom and about 1.5 inches on the top as the back of each arm is inclined to facilitate insertion into slots 36a, 36b, which are slightly larger than the arms. The second adjustment arm 58 extends behind the end of outer support arm 46b a distance of about 0.4 inches and arm 58 has a square cross-sectional area of about 0.1×0.1 inches so the bottom surface of arm 58 is about 0.1 inches below the bottom surface of support arm 46b, with the inside of the adjustment arm 58 outward of the outer side flange 26b and extending behind the bite block 20 by about 0.4 inches. The tongue depressor 54 has a generally square shape 0.7×0.7 inches so side 62 and needle guide 52 have a length of about 0.7 inches, with one truncated or angled corner having a length of about 0.4 inches which shortens side 64 of the tongue depressor plate to about 0.5 inches. The width of the first adjustment arm and leg 57 are about 0.4 inches total as they extend along the truncated corner. The needle guide is about 0.7 inches long with outer side 64 having a length about 0.4 to 0.5 inches and front side 60 having a length of about 0.6 inches. The first adjustment arm 56 extends downward about 0.2 inches beyond the bottom of the inner support arm 46a. The needle opening 68 is about $\frac{1}{16}$-inch diameter and the needle guide 52 has an inner wall with about the same inner diameter of curvature. The angles orientating the tongue depressor 54 and needle guide 52 are shown in and discussed relative to FIGS. 17-19 for the depicted embodiment and mandibular foramen.

The above dimensions and angles of the bite block 20, support plate 40, position stop 50, needle guide 52 and tongue depressor 54 believed suitable for aligning a needle tip 78 with the predetermined location of the mandibular foramen based on an average of measurements from adult, skeletal mandibles. Given the present disclosure, further refinements in predetermined locations may be similarly determined, such as the average location of the mandibular foramen of male mandibles vs female mandibles, or the mandibular foramen for children of various ages and gender. The location of the needle guide 52 and/or tongue depressor 54 may be adjusted to align the needle tip 78 with the predetermined location of the mandibular foramen. It is believed that the needle guide 52 and tongue depressor 54 will be inclined outward, rearward and downward in order to avoid gagging and to place the tongue depressor to avoid poking the tongue with the needle used to administer the anesthetic.

The location and orientation of the needle guide 52 and/or tongue depressor 54 on the support plate 40 may vary, depending in part on the location of the position stop 50 on the support plate, and the location on the anterior border of the Ramus selected for contact by the position stop. It is believed possible to specify the location and orientation of the needle guide 52 and tongue depressor 54 relative to other parts of the support plate, such as the proximal or interior end of the support arm, but because the support arm is a single part that also locates and orients the needle guide and tongue depressor relative to the position stop. Thus, for example, the depicted design has support arms 46*a*, 46*b* of equal length and the same rectangular, cross-sectional shape so it is relatively easy to specify the location and orientation of the position stop 50 relative to a fixed point on the proximal end of the outer support arm 46*a*, and specify the location and orientation of the needle guide 52 and tongue depressor 54 relative to a corresponding fixed point on the proximal end of the inner support arm 46*b*, with the two support arms providing a lateral shift between the fixed points and the support plate 40 providing fixed dimensions between the various parts connected to the support plate 40. But depending on where various parts of the support plate 40 are located on the support plate and where the support plate is connected to the bite block 20, the relative location and orientation of the position stop 50, needle guide 52 and tongue depressor 54 will change. Thus, the X, Y, Z positions and angular orientations are for the illustrated embodiment and may change with the particular configuration of the bite block and support plate.

The bite block 20 provides a stable base in a predetermined location on the patient's mandible. The alignment mechanism provided by the protrusions or recesses on the mating portions of the bite block 20 and support plate 40 (depicted as alignment slots 36 and support arms 46) allows the support plate to move relative to the bite block and position the support plate at a known location in the patient's mouth relative to the mandible and relative to a predetermined location of the mandibular foramen. Because the position of the support plate 40 is known relative to the predetermined location of the mandibular foramen, the needle guide 52 and tongue depressor 54 may be positioned to align the needle guide and coaxial needle axis with the predetermined location of the mandibular foramen while also aligning the tongue depressor to position the patient's tongue of the needle path along the needle axis.

The above description is given by way of example, and not limitation. Given the above disclosure, one skilled in the art could devise variations that are within the scope and spirit of the invention disclosed herein, including variations on the disclosed ways to configure the alignment slots 36 and support arms 46, and various ways to connect the needle guide 52 to the support plate, and various ways to connect the tongue depressor 54 to the support plate. Further, the various features of the embodiments disclosed herein can be used alone, or in varying combinations with each other and are not intended to be limited to the specific combination described herein.

What is claimed is:

1. A dental apparatus for aligning a needle tip of a syringe to administer an anesthetic in the oral cavity of a patient having a mandible with teeth thereon, comprising:
   a bite block having upper and lower teeth engaging surfaces inclined at an angle to each other and oriented in opposing directions so as to engage a portion of the upper and lower teeth, respectively, when inserted between the teeth on one side of the patient's jaws during use;
   a support plate having a front end with first and second, spaced apart support arms extending rearward during use and parallel to each other;
   the bite block including two alignment guides extending along a length of the bite block with each alignment guide being on an opposing side of the bite block, each support arm including a mating alignment guide that mates with and moves along a different one of the alignment guides, each support arm having a rear end;
   a position stop extending laterally and outward from the first support arm at a location that is behind the rear end of that first support arm;
   a needle guide connected to the second support arm and extending along a needle axis, and when the alignment guides and mating alignment guides are in mating engagement the needle guide and needle axis extend outward away from the sagittal plane, extend downward toward the mandible, and extend backward toward a location between the anterior and posterior borders of the Ramus.

2. The dental apparatus of claim 1, wherein the needle axis and needle guide are aligned to intersect a predetermined location of a mandibular foramen.

3. The dental apparatus of claim 2, further comprising:
   a tongue depressor having a plate connected to a lower portion of the needle guide and extending forward of the needle guide;
   an inner flange and an outer flange on opposing sides of each tooth engaging surface, the flanges oriented to extend along the patient's teeth during use;
   a wall extending along a vertical plane and wherein the alignment slots are formed in opposing sides of that wall and extend in a transverse plane; and
   a support stop extending between the two support arms and located to abut an end of the wall during use to limit relative movement of the support plate relative to the bite block in the rearward direction during use.

4. The dental apparatus of claim 2, wherein the alignment guides and mating alignment guides are in mating engagement.

5. The dental apparatus of claim 1, further comprising a tongue depressor having a plate connected to a lower portion of the needle guide and extending forward of the needle guide.

6. The dental apparatus of claim 1, further comprising a handle on the front end of the support plate.

7. The dental apparatus of claim 1, further comprising a support plate stop extending between the two support arms and located to abut a portion of the bite block to limit relative movement of the support plate relative to the bite block in the rearward direction when the alignment guides and mating alignment guides are in mating engagement.

8. The dental apparatus of claim 1, wherein the alignment guides and mating alignment guides are in mating engagement.

9. The dental apparatus of claim 1, further comprising an inner flange and an outer flange on opposing sides of each of the upper and lower teeth engaging surfaces, the flanges oriented to extend along the patient's teeth during use.

10. The dental apparatus of claim 9, wherein the bite block has a wall extending in a vertical plane and wherein the alignment guides comprise two slots with one slot formed in each opposing side of that wall, the two slots being parallel and extending rearward along a length of the wall.

11. The dental apparatus of claim 10, wherein each support arm has a generally rectangular cross-section which forms part of the mating alignment guide and wherein the alignment slots have a size and cross-sectional shape that mates with that rectangular cross-section.

12. The dental apparatus of claim 11, wherein the mating alignment portions of the support arms are located in the alignment slots of the bite block.

13. The dental apparatus of claim 9, further comprising a tongue depressor having a plate connected to a lower portion of the needle guide and extending forward of the needle guide.

14. A dental apparatus for aligning a needle tip of a syringe with a patient's mandible to administer an anesthetic to the patient, the mandible having teeth thereon, comprising:
- a bite block having an upper and lower teeth engaging surfaces inclined at an angle to each other and facing in opposing directions, the tooth engaging surfaces being in a first plane;
- a wall extending along the first plane and connected to at least the lower teeth engaging surface;
- two alignment slots extending along a length of the bite block and parallel to the lower teeth engaging surface and located on opposing sides of the wall;
- a support plate having first and second, spaced apart support arms each configured to engage and slide along a different one of the alignment slots, each support arm having a length;
- a position stop extending outward from a rear portion of the first support arm and extending a distance sufficient to engage an anterior border of the patient's Ramus during use; and
- a needle guide extending from the second support arm along a needle axis inclined toward the rear of the support plate and inclined downward relative to the support plate.

15. The dental apparatus of claim 14, further comprising a tongue depressor plate connected to a lower side of the needle guide and extending forward of the needle guide.

16. The dental apparatus of claim 15, wherein the tongue depressor plate has an upper surface with an outer flange extending above the upper surface along an outer length of the tongue depressor and extending to the needle guide, the outer flange not blocking the needle guide so a needle may pass through the needle guide during use.

17. The dental apparatus of claim 15, further comprising a handle connected to a forward end of the support plate.

18. The dental apparatus of claim 15, wherein the two support arms of the support plate are each located in a different one of the alignment slots, with the needle guide extending outward away from the first plane, extending in a direction downward below the support plate, and also extending in a backward direction.

19. The dental apparatus of claim 15, wherein the needle guide is offset below a bottom, back end of the second support arm by an adjustment arm.

20. The dental apparatus of claim 15, wherein each support arm slidably engages a different one of the alignment slots.

* * * * *